(12) United States Patent
Johnson et al.

(10) Patent No.: US 8,507,707 B2
(45) Date of Patent: Aug. 13, 2013

(54) REGIOSELECTIVE CATALYTIC CONVERSION OF HYDROCARBONS TO VERSATILE SYNTHETIC REAGENTS VIA C-H BOND FUNCTIONALIZATION

(75) Inventors: Samuel A. Johnson, Windsor (CA); Meghan E. Doster, Belle River (CA); Jillian A. Hatnean, Windsor (CA)

(73) Assignee: University of Windsor, Windsor (CA)

( * ) Notice: Subject to any disclaimer, the term of this patent is extended or adjusted under 35 U.S.C. 154(b) by 313 days.

(21) Appl. No.: 13/067,166

(22) Filed: May 13, 2011

(65) Prior Publication Data

US 2011/0282087 A1 Nov. 17, 2011

Related U.S. Application Data

(60) Provisional application No. 61/344,047, filed on May 13, 2010.

(51) Int. Cl.
*C07F 7/00* (2006.01)
(52) U.S. Cl.
USPC .............................. 556/95; 556/478
(58) Field of Classification Search
USPC .................................. 556/11, 478
See application file for complete search history.

(56) References Cited

PUBLICATIONS

Yoshida et al., Chemical Communications, pp. 1980-1981 (2004).*
Bartolin et al., Organometallics, vol. 25, No. 20, pp. 4738-4740 (2006).*
Balcells, D.; Clot, E.; Eisenstein, O. Chem. Rev. 2010, 110, 749-823.
McGlacken, G. P.; Bateman, L. M. Chem. Soc. Rev. 2009, 38, 2447-2464.
Kakiuchi, F.; Murai, S. Acc. Chem. Res. 2002, 35, 826-834.
Kalyani, D.; Sanford, M. S. Top. Organomet. Chem. 2007, 24, 85-116.
Girt, R.; Shi, B.-F.; Engle, K. M.; Maugel, N.; Yu, J.-Q. Chem. Soc. Rev. 2009, 38, 3242-3272.
Boutadla, Y.; Davies, D. L.; MacGregor, S. A.; Poblador-Bahamonde, A. I. Dalton Trans. 2009, 5820-5831.
Colby, D. A.; Bergman, R. G.; Ellman, J. A. Chem. Rev. 2010, 110, 624-655.
Lewis, J. C.; Bergman, R. G.; Ellman, J. A. Acc. Chem. Res. 2008, 41, 1013-1025.
Campos, K. R. Chem. Soc. Rev. 2007, 36, 1069-1084.
Fekl, U.; Goldberg, K. I. Adv. Inorg. Chem. 2003, 54, 259-320.
Jones, W. D. Acc. Chem. Res. 2003, 36, 140-146.
Jia, C.; Kitamura, T.; Fujiwara, Y. Acc. Chem. Res. 2001, 34, 633-639.
Bergman, R. G. Nature 2007, 446, 391-393.
Daugulis, O.; Zaitsev, V. G.; Shabashov, D.; Pham, Q.-N.; Lazareva, A. Synlett 2006, 20, 3382-3388.
Dick, A. R.; Sanford, M. S. Tetrahedron 2006, 62, 2439-2463.
Davies, H. M. L.; Beckwith, R. E. J. Chem. Rev. 2003, 103, 2861-2903.
Ritleng, V.; Sirlin, C.; Pfeffer, M. Chem. Rev. 2002, 102, 1731-1769.
Crabtree, R. H. J. Chem. Soc., Dalton Trans. 2001, 2437-2450.
Sen, A. Acc. Chem. Res. 1998, 31, 550-557.
Labinger, J. A.; Becraw, J. E. Nature 2002, 417, 507-514.

(Continued)

*Primary Examiner* — Porfirio Nazario Gonzalez

(57) ABSTRACT

The present invention provides a novel and improved method of functionalizing a C—H bond of an arene compound comprising the step of reacting an organometallic compound having a group 14 element with the arene compound having at least one hydrogen bonded to a carbon in the presence of a catalyst.

23 Claims, 3 Drawing Sheets

(56) References Cited

PUBLICATIONS

Shilov, A. E.; Shul'Pin, G. B. Chem. Rev. 1997, 97, 2879-2932.
Arndtsen, B. A.; Bergman, R. G.; Mobley, T. A.; Peterson, T. H. Acc. Chem. Res. 1995, 28, 154-162.
Ryabov, A. D. Chem. Rev. 1990, 90, 403-424.
Yu, J.-Q.; Giri, R.; Chen, X. Org. Biomol. Chem. 2006, 4, 4041-4047.
Lyons, T. W.; Sanford, M. S. Chem. Rev. 2010, 110, 1147-1169.
Mkhalid, I. A. I.; Barnard, J. H.; Marder, T. B.; Murphy, J. M.; Hartwig, J. F. Chem. Rev., 110, 890-931, (2010).
Alberico, D.; Scott, M. E.; Lautens, M. Chem. Rev. 2007, 107, 174-238.
Chen, X.; Engle, K. M.; Wang, D.-H.; Yu, J.-Q. Angew. Chem., Int. Ed. 2009, 48, 5094-5115.
Daugulis, O.; Do, H.-Q.; Shabashov, D. Acc. Chem. Res. 2009, 42, 1074-1086.
Crabtree, R. H. Chem. Rev. 1985, 85, 245-269.
Li, B.-J.; Yang, S.-D.; Shi, Z.-J. Synlett 2008, 7, 949-957.
Thansandote, P.; Lautens, M. Chem—Eur. J. 2009, 15, 5874-5883.
Hartwig, J. F. Nature 2008, 455, 314-322.
Beccalli, E. M.; Broggini, G.; Martinelli, M.; Sottocornola, S. Chem. Rev. 2007, 107, 5318-5365.
Deprez, N. R.; Sanford, M. S. Inorg. Chem. 2007, 46, 1924-1935.
Godula, K.; Sames, D. Science 2006, 312, 67-72.
Corbet, J.-P.; Mignani, G. Chem. Rev. 2006, 106, 2651-2710.
Hagmann, W. K. J. Med. Chem. 2008, 51, 4359-4369.
Jeschke, P. Pest Manage. Sci. 2009, 66, 10-27.
Muller, K.; Faeh, C.; Diederich, F. Science 2007, 317, 1881-1886.
Purser, S.; Moore, P. R.; Swallow, S.; Gouverneur, V. Chem. Soc. Rev. 2008, 37, 320-330.
Begue, J.-P.; Bonnet-Delpon, D. J. Fluorine Chem. 2006, 127, 992-1012.
Brooke, G. M. J. Fluorine Chem. 1997, 86, 1-76.
Shimizu, M.; Hiyama, T. Angew. Chem., Int. Ed. 2005, 44, 214-231.
Watson, D. A.; Su, M.; Teverovskiy, G.; Zhang, Y.; Garcia-Fortanet, J.; Kinzel, T.; Buchwald, S. L. Science 2009, 325, 1661-1664.
Prakash, G. K. S.; Chacko, S. Curr. Opin. Drug Discovery Dev. 2008, 11, 793-802.
Amii, H.; Uneyama, K. Chem. Rev. 2009, 109, 2119-2183.
Schaub, T.; Backes, M.; Radius, U. J. Am. Chem. Soc. 2006, 128, 15964-15965.
Do, H.-Q.; Daugulis, O. J. Am. Chem. Soc. 2008, 130, 1128-1129.
Lafrance, M.; Rowley, C. N.; Woo, T. K.; Fagnou, K. J. Am. Chem. Soc. 2006, 128, 8754-8756.
Lafrance, M.; Shore, D.; Fagnou, K. Org. Lett. 2006, 8, 5097-5100.
Nakao, Y.; Kashihara, N.; Kanyiva, K. S.; Hiyama, T. J. Am. Chem. Soc. 2008, 130, 16170-16171.
Stuart, D. R.; Fagnou, K. Science 2007, 316, 1172-1175.
Cho, J.-Y.; Iverson, C. N.; Smith, M. R., III J. Am. Chem. Soc. 2000, 122, 12868-12869.
Farina, V.; Krishnamurthy, V.; Scott, W. J. Org. React. 1997, 50.
Espinet, P.; Echavarren, A. M. Angew. Chem., Int. Ed. 2004, 43, 4704-4734.
Deacon, G. B.; Gatehouse, B. M.; Nelson-Reed, K. T. J. Organomet. Chem. 1989, 359, 267-283.
Miller, J. M.; Chivers, T.; Lanthier, G. F. J. Chem. Soc. A 1971, 2556-2563.
Chivers, T.; Sams, J. R. J. Chem. Soc. A 1970, 928-931.
Chiver, T.; Sams, J. R. Chem. Commun. 1969, 249-250.
Robichaud, A. J.; Lee, T.; Deng, W.; Mitchell, I. S.; Haydar, S.; Chen, W.; McClung, C. D.; Calvello, E. J. B.; Zawrotny, D. M. PCT Int. Appl. 2000, 764 pp.
Inoue, M.; Tsuzuki, T.; Fujimoto, T.; Yamamoto, I. Jpn. Kokai Tokkyo Koho 2007, 11pp.
Li, H.; Li, L.; Schwartz, D. J.; Metz, M. V.; Marks, T. J.; Liable-Sands, L.; Rheingold, A. L. J. Am. Chem. Soc. 2005, 127, 14756-14768.
Deeter, G. A.; Moore, J. S. Macromolecules 1993, 26, 2535-2541.
McAdon, M. H.; Nickias, P. N.; Marks, T. J.; Swartz, D. J. PCT Int. Appl. 1999, 37 pp.
Coates, G. E. et al. Organometallic Compounds, vol. One. The Main Group Elements, Part Two: Groups IV and V; 4th ed.; John Wiley and Sons: New York, 1979.
Jenkins, A. D.; Lappert, M. F.; Srivastava, R. C. J. Organomet. Chem. 1970, 23, 165-172.

\* cited by examiner

REGIOSELECTIVE CATALYTIC CONVERSION OF HYDROCARBONS TO VERSATILE SYNTHETIC REAGENTS VIA C-H BOND FUNCTIONALIZATION

RELATED APPLICATIONS

This application claims benefit under 35 U.S.C., §119(e) to U.S. Provisional application No. 61/344,047 filed on May 13, 2010.

SCOPE OF THE INVENTION

The present invention relates to a novel and improved method for catalytic functionalization of a C—H bond. More particularly, the present invention relates to a novel and improved method of functionalizing a C—H bond of an arene compound having at least one hydrogen bonded to a carbon, the method comprising a single step of reacting the arene compound with an organometallic compound having a group 14 element.

BACKGROUND OF THE INVENTION

Methods of forming a C—C bond between two different compounds each having a C—H bond continues to be of keen interest to the pharmaceutical and fine chemical industries. Namely, the formation of the C—C bond by first breaking the two C—H bonds and then forming a bond between the two carbons is particularly desirable given ready accessibility of hydrocarbon compounds, atom efficiency, and reduced production cost. The formation of the C—C bond may be illustrated by the following chemical equation:

$R_1$—C—H+H—C—$R_2$→$R_1$—C—C—$R_2$

Methods of forming C—C bonds from C—H bonds are known to be difficult as C—H bonds are only modestly reactive under mild conditions. One way to overcome the difficulty is to introduce an intermediate step of first functionalizing or "activating" the C—H bond using a transition metal catalyst and then reacting the functionalized C—H bond with another compound. Functionalization of the C—H bond involves substituting the hydrogen atom with a different functional group. Preferably, the functional group forms a more reactive bond with the carbon such that the carbon becomes more reactive to form different chemical bonds in subsequent reactions.

To date, functionalization of C—H bonds have focused primarily on formation of C—B, C—C, C—N, and C—O bonds with much less attention paid to coupling the carbon to heavier atoms. For example, one of the most commonly used methods involves formation of a C—B bond by use of boron chemistry. The "functionalized" C—B bond may subsequently be utilized in a Imamura-Suzuki coupling reaction to create a C—C bond as exemplified in the following chemical equation where each of $R_1$ and $R_2$ comprises a hydrocarbon moiety:

$R_1$—$BY_2$ + $R_2$—X $\xrightarrow[\text{Base}]{\text{Pd catalyst}}$ $R_1$—$R_2$ The foregoing use of boron chemistry to create the C—C bond suffers a number of disadvantages including low product yields and limited scope of application, especially in the presence of incompatible functional groups. It is therefore desirable to have a new and improved method to functionalize a C—H bond which avoids the disadvantages of boron chemistry.

It is of note that a new and improved method to functionalize a C—H bond would have valuable applications in synthesis of fluorinated compounds. Fluorinated compounds are considered to be important compounds in the pharmaceutical and agrochemical sectors due to their increased resistance to metabolic degradation and increased lipophilicity. Fluorinated compounds also find use as important parts in a number of polymers, membrane, and semi-conductor materials.

Traditionally, to synthesize a particular fluorinated compound, fluorination is performed at a final stage of chemical synthesis to convert a non-fluorinated intermediate to the desired fluorinated compound. Such approach suffers the disadvantages of being limited by the chemistry of fluorination and the high costs associated with fluorination. Therefore, it would be advantageous to instead begin the synthesis with a fluorinated intermediate, and then subject the fluorinated intermediate to subsequent reactions to obtain the desired fluorinated compound. Such approach is particularly advantageous as a number of fluorinated intermediates or starting compounds are commercially available.

To synthesize the desired fluorinated compound from the fluorinated intermediate, the subsequent reactions may advantageously incorporate functionalization of a C—H bond of the fluorinated intermediate. For example, the C—H bond may be functionalized and converted to a C—Sn bond. The carbon of the C—Sn bond may subsequently be utilized in a well-developed Stille coupling reaction to form a bond with another carbon as exemplified in the following chemical reaction where each of R and R' comprises a hydrocarbon moiety:

R—$Sn(R)_3$+R'—X→R—R'+X—$Sn(R)_3$

Such combination of functionalization of a C—H bond and subsequent reaction of the functionalized bond to form a C—C bond may readily be incorporated as part of synthesis of a wide variety of commercially useful fluorinated compounds.

Currently, a number of fluorinated intermediate compounds with a functionalized C—Sn bond are commercially available. Such compounds include 2,3,4,5,6-pentafluorophenyltrimethylstannane and bis(pentafluorophenyl)dimethylstannane. Other fluorinated intermediate compounds such as 2,3,5,6-tetrafluorophenyltrimethylstannane, 2,3,4,6-tetrafluorophenyltrimethylstannane, and (2,3,4-trifluorophenyl)trimethylstannane are known but are not commercially available on any reasonable scale. Such fluorinated compounds are often made using methods that are expensive (and involving use of organomagnesium, organolithium and organotinhalide compounds), leads to a limited range of products, and which involve multiple steps performed at high temperatures with poor product yield.

Therefore, it is desirable to find a novel and improved method to synthesize fluorinated intermediate compounds with a functionalized C—Sn bond, which is simple and commercially viable with high product yields and which avoids use of expensive and harmful reagents.

SUMMARY OF THE INVENTION

The applicant having conducted extensive studies and research have unexpectedly discovered that a C—H bond of an arene compound may be selectively functionalized by reaction with an organometallic compound having a group 14 element. Particularly, the applicant has unexpectedly discovered that a C—H bond of a fluorinated compound could be functionalized in a single step without also functionalizing the C—F bonds.

It is therefore an object of the present invention is to provide a novel and improved method of functionalizing a C—H bond of an organic compound, which overcomes the disadvantages noted above, and which may be performed in a relatively straightforward manner in a single step using commercially available compounds and requiring lower energy input and costs.

A further object of the present invention is to provide a novel and improved method of functionalizing a C—H bond of an organic compound preferably an aromatic compound and more preferably a fluorinated aromatic compound, which avoids use of organomagnesium, organolithium and organotinhalide compounds, and to minimize harmful reaction intermediates or by-products.

A further object of the present invention is to provide a novel and improved method for functionalizing a C—H bond of a fluorinated organic or arene compound, which is readily incorporated into multi-step synthesis for a wide variety of fluorinated organic or arene compounds, and which avoids the limitation of fluorination chemistry and associated high costs.

A further object of the present invention is to provide a novel and improved method of functionalizing a C—H bond of an organic compound by formation of a C—Sn bond, which is readily utilized in a Stille coupling reaction to form a C—C bond with greater yield and wider application when compared to Imamura-Suzuki coupling reaction.

In one simplified aspect, the invention provides a novel and improved method of functionalizing a C—H bond of an arene compound, and more preferably a fluorinated arene compound, comprising the step of reacting a first organometallic compound with the arene compound in the present of a catalyst, wherein said first organometallic compound comprises a group 14 element, and said arene compound comprises at least one hydrogen bonded to a carbon.

Preferably, the first organometallic compound is an organotin compound. The organotin compound may have but not limited to the chemical formula $R_3SnR^1$, wherein each of R and $R^1$ comprises a functional group or moiety. The R group may preferably be but not limited to a methyl group (Me) or a butyl group (Bu). The $R^1$ group may preferably be but not limited to a vinyl group or a propenyl group which may include a functional group or moiety attached thereto. Good reactivity and high product yields have been demonstrated with the organotin compound of formula $R_3SnR^1$, wherein the R group is a methyl or butyl group and $R^1$ group is a vinyl or propenyl group, or namely $Me_3Sn(CH=CH_2)$, $Bu_3Sn(CH=CH_2)$, $Me_3Sn(CH=CHCH_3)$ and $Bu_3Sn(CH=CHCH_3)$. $Bu_3Sn(CH=CH_2)$ is particularly preferred in the method of the present invention due to its commercial availability.

Alternatively, the first organometallic compound may preferably be an organosilane compound. The organosilane compound may have but not limited to the chemical formula $R^2{}_3SiR^3$, wherein each of $R^2$ and $R^3$ comprises a functional group or moiety. The method of the present invention has been demonstrated to work with the preferred $R^2$ such as a phenyl group, a hydrogen or any combinations thereof, and the preferred $R^3$ such as a hydrogen.

Alternatively, the reagent may also preferably be an organogermanium compound or an organolead compound.

The arene compound may be a heterocyclic compound. Preferred heterocyclic compounds include pyridine, pyrazine, imidazole, pyrazole, oxazole, and thiophene. More preferably, the arene compound comprise a benzene. Most preferred arene compounds include fluorinated benzenes such as fluorobenzene, 1,2-difluorobenzene, 1,3-difluorobenzene, 1,4-difluorobenzene, 1,2,3-trifluorobenzene, 1,2,4-trifluorobenzene, 1,3,5-trifluorobenzene, 1,2,3,4-tetrafluorobenzene, 1,2,3,5-tetrafluorobenzene, 1,2,4,5-tetrafluorobenzene, and pentafluorobenzene. As well, more reactive fluorinated benzenes, such as 1,3-difluorobenzene, 1,2,4-trifluorobenzene, 1,3,5-trifluorobenzene, 1,2,3,5-tetrafluorobenzene, 1,2,4,5-tetrafluorobenzene, and pentafluorobenzene, which has a hydrogen substituent adjacent to two fluorine substituents, are more particularly preferred.

Preferably, the arene compound comprises a substituent other than hydrogen. The substituent may include but not limited to a fluorine, a trifluoromethyl group and other directing groups. The method of the present invention has been demonstrated to work with a number of fluorinated arene compounds.

The catalyst is not particularly limited, and is selected to be capable of catalyzing functionalization of the C—H bond of the arene compound. Preferably, the catalyst comprises at least one of a second organometallic compound and an ancillary ligand. The ancillary ligand may be a chelating ligand or a multidentate ligand, and are preferably selected from $PCy_3$, $P^iPr_3$, $PEt_3$ and $MeNC_5H_4N^iPr$, wherein Cy is a cyclohexyl group, Et is an ethyl group and $^iPr$ is a isopropyl group. The structural formula of the aforementioned $MeNC_5H_4N^iPr$ is shown below:

Most preferably, the catalyst is $Ni(COD)_2$, where COD is 1,5-cyclooctadiene. $Ni(COD)_2$ either alone or in combination with at least one of $PCy_3$, $P^iPr_3$, $PEt_3$ and $MeNC_5H_4N^iPr$ as the ancillary ligand is most preferred.

The method of the present invention may be performed neat or in a solvent. The solvent may preferably be an organic solvent including but not limited to pentane, benzene and toluene. The temperature of the method of the present invention is not particularly limited but preferably performed under 100° C., and most preferably between 25° C. to 45° C. The pressure to be used in the method of the present invention is also not particularly limited. Conveniently, the method may be carried out in a sealed NMR tube.

The method of the present invention is not particularly limited with respect to the relative amounts of the first organometallic compound, the arene compound, and the catalyst. Preferably, the catalyst is added in an amount which is 1 to 10 percent of the molar amount of either the first organometallic compound or the arene compound. More preferably, the amount of the catalyst is between 3 to 8 percent of the molar amount of either the first organometallic compound or the arene compound.

The method of the present invention may be used to functionalize more than one C—H bonds of the arene compound if the arene compound contains more than one C—H bonds. To functionalize more than one C—H bonds of the arene compound, for example two C—H bonds, it is preferable to perform the method with the first organometallic compound in an amount which is twice or more of the molar amount of the arene compound. To functionalize for example three C—H bonds, it is preferable to perform the method with the first organometallic compound in an amount which is three times or more of the molar amount of the arene compound.

Another aspect of the present invention therefore provides a method of functionalizing a C—H bond of an arene compound comprising the step of reacting a first organometallic compound with said arene compound in the present of a catalyst, wherein said first organometallic compound comprises a group 14 element; and said arene compound comprises at least one hydrogen bonded to a carbon.

In a further aspect of the present invention, the method is carried out in a single step.

In a further aspect of the present invention, said first organometallic compound is selected from the group consisting of an organotin compound, an organosilane compound, an organogermanium compound and an organolead compound.

In yet a further aspect of the present invention, said organotin compound has the chemical formula $R_3SnR^1$, wherein each of said R is selected from the group consisting of a methyl group and a butyl group; and said $R^1$ comprises a double bond.

In a further aspect of the present invention, said double bond is adjacent to a bond between said $R^1$ and said Tin.

In a further aspect of the present invention, said $R^1$ is selected from the group consisting of a vinyl group and a propenyl group.

In a further aspect of the present invention, said organotin compound is selected from the group consisting of $Me_3Sn(CH\!=\!CH_2)$, $Bu_3Sn(CH\!=\!CH_2)$, $Me_3Sn(CH\!=\!CHCH_3)$ and $Bu_3Sn(CH\!=\!CHCH_3)$, wherein said Me is the methyl group and said Bu is the butyl group.

In a further aspect of the present invention, said organosilane compound has the chemical formula $R^2{}_3SnH$, wherein each of said $R^2$ is selected from the group consisting of a phenyl group and a hydrogen.

In a further aspect of the present invention, said arene compound is a heterocyclic compound.

In a further aspect of the present invention, said arene compound has as a substituent a fluorine.

In a further aspect of the present invention, said arene compound is benzene.

In a further aspect of the present invention, said benzene has as a substituent a fluorine.

In a further aspect of the present invention, said hydrogen is adjacent to two of said fluorine.

In a further aspect of the present invention, said benzene is selected from the group consisting of 1,2-difluorobenzene, 1,3-difluorobenzene, 1,4-difluorobenzene, 1,2,3-trifluorobenzene, 1,2,4-trifluorobenzene, 1,3,5-trifluorobenzene, 1,2,3,4-tetrafluorobenzene, 1,2,3,5-tetrafluorobenzene, 1,2,4,5-tetrafluorobenzene, and pentafluorobenzene.

In a further aspect of the present invention, said catalyst comprises at least one of a second organometallic compound and an ancillary ligand.

In a further aspect of the present invention, said second organometallic compound comprises an element selected from the group consisting of nickel and mercury.

In a further aspect of the present invention, said ancillary ligand comprises at least one of $PCy_3$, $P^iPr_3$, $PEt_3$ and $MeNC_5H_4N^iPr$, wherein said Cy is a cyclohexyl group; said $^iPr$ is a isopropyl group; said Et is an ethyl group; said Me is a methyl group; and said $MeNC_5H_4N^iPr$ has the following structural formula:

In a further aspect of the present invention, said second organometallic compound comprises $Ni(COD)_2$, wherein COD is 1,5-cyclootadiene.

In a further aspect of the present invention, said step is carried out with a first molar amount of said reagent and a second molar amount of said organic compound, wherein said first molar amount is stoichiometrically equivalent to said second molar amount.

In a further aspect of the present invention, said first molar amount is greater than said second molar amount.

In a further aspect of the present invention, said first molar amount is less than said second molar amount.

In a further aspect of the present invention, said step is carried out at a temperature lower than 100° C.

In a further aspect of the present invention, said temperature is between 25° C. to 45° C.

In a further aspect of the present invention, said step is carried out in an organic solvent selected from the group consisting of pentane, benzene, and toluene.

In a further aspect of the present invention, said step is carried out without solvent.

BRIEF DESCRIPTION OF THE DRAWINGS

Reference may now be had to the following detailed description, taken together with the accompanying drawings, in which.

DETAILED DESCRIPTION OF THE PREFERRED EMBODIMENTS

The most preferred embodiments of the present invention are henceforth described with reference to FIGS. 1 to 3. The most preferred embodiments are provided as mere examples which are in no way intended to limit the scope of the present invention. It will be readily apparent to a person skilled in the art that variations and modifications may be made to the most preferred embodiments within the scope of the present invention.

In a first example process, a single-step catalytic stannylation of a fluorinated arene compound was achieved using $Bu_3Sn(CH\!=\!CH_2)$ or $Me_3Sn(CH\!=\!CH_2)$ as a first organometallic compound in the presence of $Ni(COD)_2$ with at least one of $MeNC_5H_4N^iPr$ and $P^iPr_3$ as a catalyst as follows:

The preferred reaction advantageously shows quantitative functionalization and may be performed using as little as 1 mol % of Ni(COD)$_2$ and MeNC$_5$H$_4$N$^i$Pr to go to completion. Test reactions were run at room temperature and yielded ethylene as a by-product. The reaction may further be performed without addition of solvent.

In test samples the above reaction has been demonstrated to work with a number of different fluorinated arene compounds yielding resulting functionalized products in excess of 90%.

Table 1 below illustrates example single-step reactions of the present invention involving use of fluorinated arene compounds having 2 to 5 fluorine substituents, the catalyst Ni(COD)$_2$ and the ancillary ligand MeNC$_5$H$_4$N$^i$Pr and/or P$^i$Pr$_3$. The yield percent marked with the superscript a provides NMR yield from integration of $^{19}$F[$^1$H] NMR spectra, and yield percent marked with the superscript b provides isolated yield after chromatography. The condition hours marked with the superscript c and d denote that the reaction was carried out using 2.5 molar amount of Bu$_3$Sn(CH=CH$_2$) and 10 fold excess of the fluorinated arene compound, respectively.

TABLE 1

| Reagent | Ancillary Ligand and Ni(COD)$_2$ Loading (%) | Conditions | Yield (%) | Products | # |
|---|---|---|---|---|---|
| C$_6$F$_5$H | MeNC$_5$H$_4$N$^i$Pr 3%<br>P$^i$Pr$_3$, 5% | 35° C., 1 h<br>80° C., 3 h | 95$^a$ (70$^b$)<br>98$^a$ | Bu$_3$Sn-C$_6$F$_5$ (pentafluorophenyl-SnBu$_3$) | 1 |
| 1,2,4,5-C$_6$F$_4$H$_2$ | MeNC$_5$H$_4$N$^i$Pr 3%<br>P$^i$Pr$_3$, 5% | 35° C., 0.5 h<br>80° C., 0.2 h | 95$^a$ (4$^a$ of 3)<br>93$^a$ (7$^a$ of 3) | Bu$_3$Sn-(2,3,5,6-tetrafluorophenyl) | 2 |
| 1,2,4,5-C$_6$F$_4$H$_2$ | MeNC$_5$H$_4$N$^i$Pr 3%<br>P$^i$Pr$_3$, 5% | 45° C., 6 h$^c$<br>80° C., 8 h$^c$ | 85$^a$ (11 of 2)<br>99$^a$ | Bu$_3$Sn-(tetrafluorophenylene)-SnBu$_3$ | 3 |
| 1,2,3,5-C$_6$F$_4$H$_2$ | MeNC$_5$H$_4$N$^i$Pr 3%<br>P$^i$Pr$_3$, 5% | 35° C., 0.7 h<br>80° C., 0.5 h | 95$^a$ (82$^b$)<br>90$^a$ (10 of 5) | Bu$_3$Sn-(2,3,4,6-tetrafluorophenyl) | 4 |
| 1,2,3,5-C$_6$F$_4$H$_2$ | MeNC$_5$H$_4$N$^i$Pr 5%<br>P$^i$Pr$_3$, 5% | 40° C., 18 h$^c$<br>80° C., 12 h$^c$ | 84$^a$ (12 of 4)<br>99$^a$ | Bu$_3$Sn-(tetrafluorophenylene)-SnBu$_3$ | 5 |

TABLE 1-continued

| Reagent | Ancillary Ligand and Ni(COD), Loading (%) | Conditions | Yield (%) | Products | # |
|---|---|---|---|---|---|
| 1,2,3,4-$C_6F_4H_2$ | MeN$C_5H_4N^iPr$ 3%<br>$P^iPr_3$, 5% | 45° C., 12 h<br>80° C., 4 h | 38[a]<br>95[a] |  | 6 |
| 1,2,4-$C_6F_43H_{23}$ | MeN$C_5H_4N^iPr$ 3%<br>$P^iPr_3$, 5% | 35° C., 7 h<br>80° C., 1 h | 98[a]<br>98[a] |  | 7 |
| 1,2,4-$C_6F_43H_{23}$ | $P^iPr_3$, 5% | 80° C., 48 h[c] | 50[a]<br>(40[a] of 7 and $Bu_6Sn_2$) |  | 8 |
| 1,3,5-$C_6F_43H_{23}$ | MeN$C_5H_4N^iPr$ 3%<br>$P^iPr_3$, 5% | 40° C., 4 h<br>80° C., 0.5 h | 91[a] (83[b])<br>83[a] (17 of 11) |  | 10 |
| 1,3,5-$C_6F_43H_{23}$ | MeN$C_5H_4N^iPr$ 5%<br>$P^iPr_3$, 5% | 40° C., 18 h[c]<br>80° C., 12 h[c] | 38[a] (55 of 10)<br>45[a] (50 of 12) |  | 11 |
| 1,3,5-$C_6F_43H_{23}$ | $P^iPr_3$, 5% | 80° C., 18 h[d] | 95[a] (5 of 11) |  | 12 |
| 1,2,3-$C_6F_43H_{23}$ | $P^iPr_3$, 5% | 80° C., 48 h | 50[a] (30 of 14) |  | 13 |
| 1,2,3-$C_6F_43H_{23}$ | $P^iPr_3$, 5% | 80° C., 18 h[c] | 30[a]<br>(40 of 13 and $Bu_6Sn_2$) |  | 14 |

TABLE 1-continued

| Reagent | Ancillary Ligand and Ni(COD), Loading (%) | Conditions | Yield (%) | Products | # |
|---|---|---|---|---|---|
| 1,3-$C_6F_{42}H_{24}$ | $P^iPr_3$, 5% | 80° C., 18 h | 90$^a$ | $Bu_3Sn$–(2,6-difluorophenyl) | 15 |
| 1,2-$C_6F_{42}H_{24}$ | $P^iPr_3$, 5% | 80° C., 72 h$^e$ | 92$^a$ (2 of 17) | $Bu_3Sn$–(2,3-difluorophenyl) | 16 |
| 1,4-$C_6F_{42}H_{24}$ | $P^iPr_3$, 5% | 80° C., 18 h$^e$ | 90$^a$ (10 of 19) | $Bu_3Sn$–(2,5-difluorophenyl) | 18 |
| 2,3,5,6-$C_6F_4HN$ | $P^iPr_3$, 5% | 80° C., 2 h | 98$^a$ (87$^b$) | $Bu_3Sn$–(2,3,5,6-tetrafluoropyridyl) | 22 |

Figure 1:
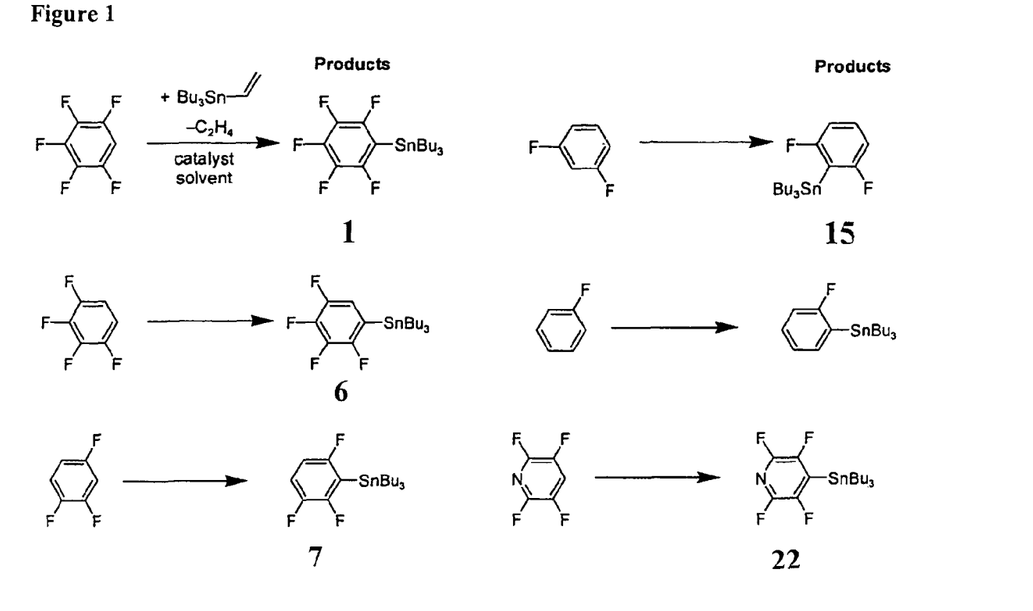
FIG. 1 illustrates the chemical equations of the most preferred methods of the present invention, which involves mono-functionalization of a flourinated benzene or pyridine containing 1 to 5 fluorine substituents with $Bu_3Sn(CH\!=\!CH_2)$ in the presence of a catalyst.
Figure 2:
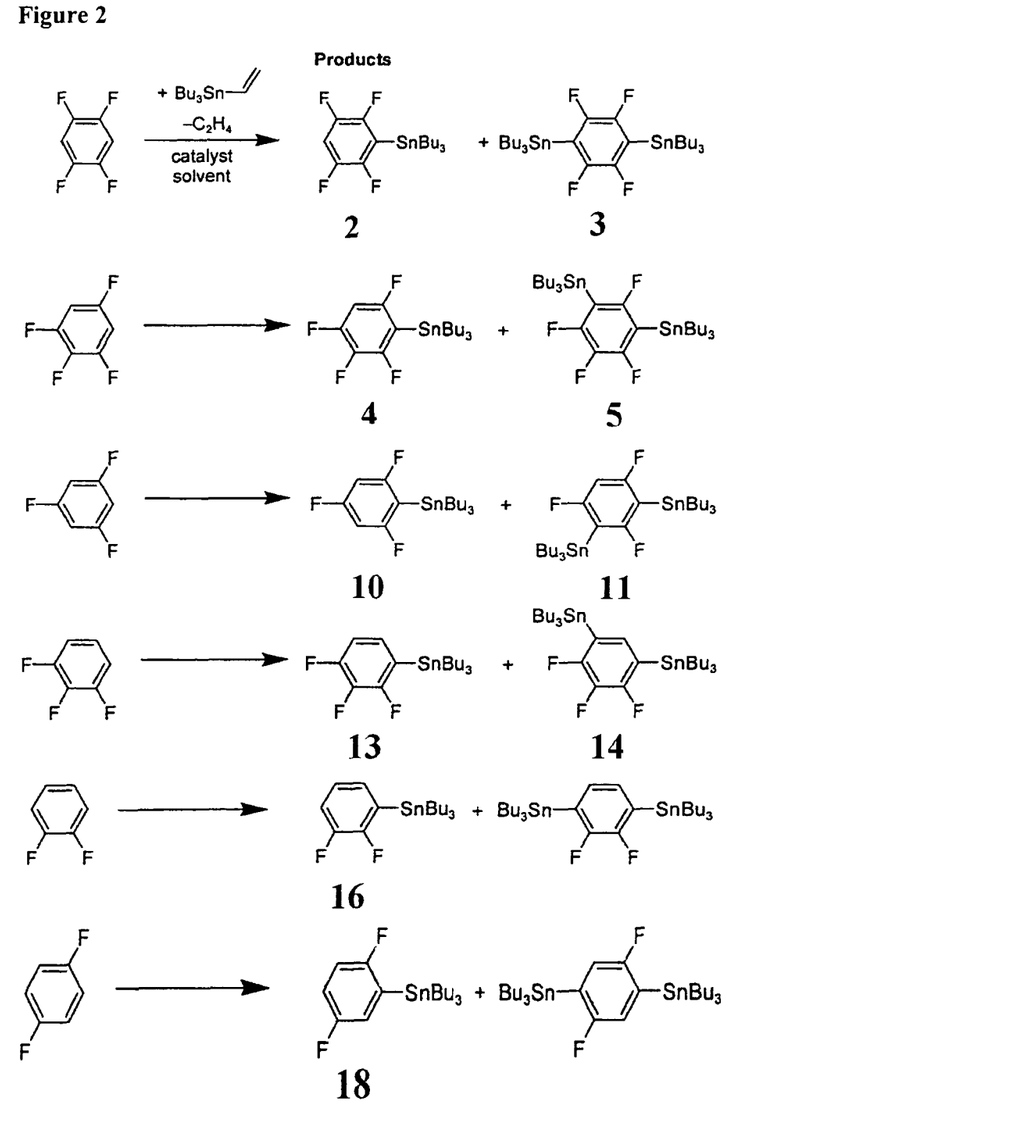
FIG. 2 illustrates the chemical equations of the most preferred methods of the present invention, which involves both mono-functionalization and di-functionalization of a fluorinated benzene containing 2 to 4 fluorine substituents with $Bu_3Sn(CH\!=\!CH_2)$ in the presence of a catalyst.

FIGS. 1 and 2 provide the chemical equations for production of the specific functionalized or stannylated fluorinated arene compounds numerically identified in Table 1 above. It has been discovered that arene compounds with C—H bonds that are adjacent to two C—F bonds such as 1,3-difluorobenzene, 1,2,4-trifluorobenzene, 1,3,5-trifluorobenzene, 1,2,3,5-tetrafluorobenzene, 1,2,4,5-tetrafluorobenzene, and pentafluorobenzene are most reactive.

The monostannylated compounds 1, 2, 4, 7 and 10 were obtained with good selectivity (above 91%) using a modest excess of the fluorinated arene compound (about two times the molar amount); the only significant impurities were the distannylated fluorinated arene compounds 3, 5, 8, and 11 which were readily separated. The distannylated fluorinated arene compounds could be obtained with good selectivity by using 2.5 times the molar amount of $Bu_3Sn(CH=CH_2)$. The tristannylated fluorinated arene compound 13 was also accessible using $P^iPr_3$ as the ancillary ligand.

Compared to data on similar or analogous functionalization by use of boron chemistry as described above, the preferred functionalization of the present invention has been demonstrated to occur under milder conditions, produce higher yields, and be more selective, with no C—F functionalization products observed.

Although use of $P^iPr_3$ as the ancillary ligand has been observed to provide lower reaction rates than that of $MeNC_5H_4N^iPr$, $P^iPr_3$ is preferable when carrying out the functionalization at higher temperatures due to improved thermal stability. For example, functionalization of 1,2,3,4-tetrafluorobenzene occurred in 4 hours at 80° C. and provided selective conversion to the monostannylated fluorinated arene compound 6. Similar results were demonstrated with the functionalization of 1,2,3-trifluorobenzene, providing the monostannylated fluorinated arene compound 13. The distannylated fluorinated arene compound 14 was also obtained selectively in the presence of excess $Bu_3Sn(CH=CH_2)$ and was present as a slight impurity in the synthesis of the monostannylated fluorinated arene compound 13. The functionalization of heterocycles such as 2,3,5,6-tetrafluoropyridine was also demonstrated using an ancillary ligand comprising a phosphine.

Figure 3:
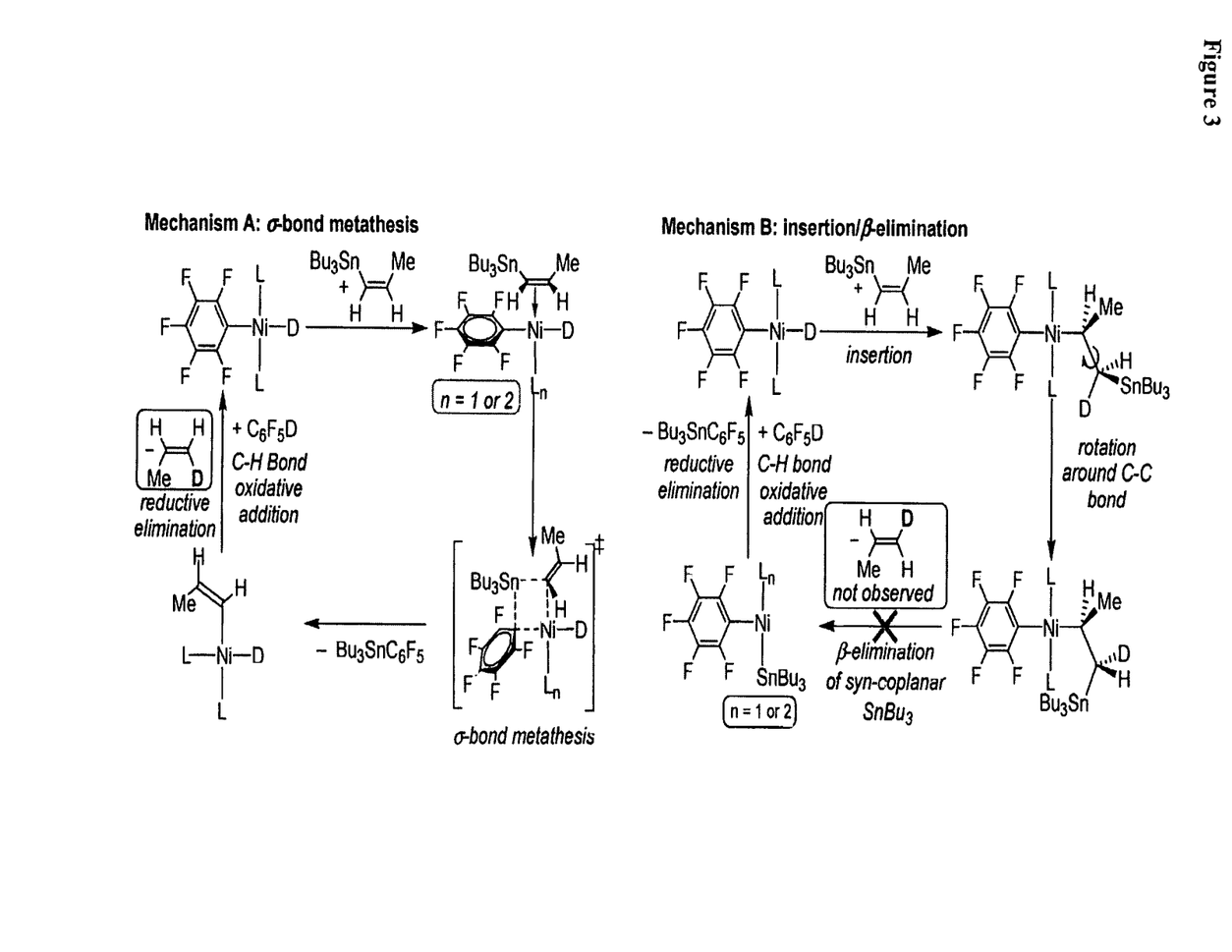
FIG. 3 illustrates examples of two different possible reaction mechanisms for the specific preferred method of functionalization of $C_6F_5D$ with cis-(1-propenyl)$SnBu_3$ in the presence of a catalyst.

Two plausible mechanistic manifolds for the preferred method of functionalizing $C_6F_5D$ with cis-(1-propenyl)$SnBu_3$ that invoke the oxidative addition product $L_2NiD(C_6F_5)$, where L is the ancillary ligand, are shown in FIG. 3. One possibility is that the reaction occurs by oxidative addition of C—H and C—Sn bonds to Ni centers, pure σ-bond metathesis, or some combination of these processes. An example of this mechanistic manifold showing oxidative addition of the C—H bond of the fluoroarene and σ-bond metathesis to form the new C—Sn bond is shown in FIG. 3 as mechanism A. In this mechanism, the double bond of the propenyl group coordinates to the metal, which brings the $Bu_3Sn$ and $C_6F_5$ substituents into close enough proximity to undergo σ-bond metathesis. Reductive elimination of (Z)-1-deuteropropene followed by oxidative addition of $C_6F_5D$ regenerates $L_2NiD(C_6F_5)$. Mechanism B involves 1,2-insertion of the vinyl moiety into the Ni-D bond followed by β-elimination of the $SnBu_3$ group. Mechanism B would produce (E)-1-deuteropropene and thus can be differentiated from mechanism A.

Experimentally, the functionalization of $C_6F_5D$ with cis-(1-propenyl)$SnBu_3$ was observed to liberate almost exclusively (Z)-1-deuteropropene at 50% conversion, as identified by ¹H NMR spectroscopy. The formation of (Z)-1-deuteropropene supports mechanistic manifold A, where oxidative addition, σ-bond metathesis, or a combination of these processes accounts for Sn—C bond formation. Mechanism A is reminiscent of Stille coupling, where the aryl group in this case adopts the role typically played by a halide anion during the transmetalation step. This reaction pathway provides an unexpected route to C—H bond functionalization under mild conditions.

We claim:

1. A method of functionalizing a C—H bond of an arene compound comprising the step of reacting a first organometallic compound with said arene compound in the presence of a catalyst, wherein:
   a. said first organometallic compound comprises a group 14 element; and
   b. said arene compound comprises at least one hydrogen bonded to a carbon.

2. The method of claim 1, wherein the method is carried out in a single step.

3. The method of claim 1, wherein said first organometallic compound is selected from the group consisting of an organotin compound, an organosilane compound, an organogermanium compound and an organolead compound.

4. The method of claim 1, wherein said organometallic compound comprises an organotin compound having the chemical formula $R_3SnR^1$, wherein:
   a. each of said R is selected from the group consisting of a methyl group and a butyl group; and
   b. said $R^1$ comprises a double bond.

5. The method of claim 4, wherein said double bond is adjacent to a bond between said $R^1$ and said Tin.

6. The method of claim 5, wherein said $R^1$ is selected from the group consisting of a vinyl group and a propenyl group.

7. The method of claim 6, wherein said organotin compound is selected from the group consisting of $Me_3Sn(CH=CH_2)$, $Bu_3Sn(CH=CH_2)$, $Me_3Sn(CH=CHCH_3)$ and $Bu_3Sn(CH=CHCH_3)$, wherein said Me is the methyl group and said Bu is the butyl group.

8. The method of claim 3, wherein said organosilane compound has the chemical formula $R^2_3SnH$, wherein each of said $R^2$ is selected from the group consisting of a phenyl group and a hydrogen.

9. The method of claim 4, wherein said arene compound is a fluorinated heterocyclic compound.

10. The method of claim 1, wherein said arene compound has as a substituent a fluorine.

11. The method of claim 4, wherein said arene compound is benzene.

12. The method of claim 11, wherein said benzene has as a substituent a fluorine.

13. The method of claim 12, wherein said hydrogen is adjacent to two of said fluorine.

14. The method of claim 12, wherein said benzene is selected from the group consisting of 1,2-difluorobenzene, 1,3-difluorobenzene, 1,4-difluorobenzene, 1,2,3-trifluorobenzene, 1,2,4-trifluorobenzene, 1,3,5-trifluorobenzene, 1,2,3,4-tetrafluorobenzene, 1,2,3,5-tetrafluorobenzene, 1,2,4,5-tetrafluorobenzene, and pentafluorobenzene.

15. The method of claim 1, wherein said catalyst comprises at least one of a second organometallic compound and an ancillary ligand.

16. The method of claim 15, wherein said second organometallic compound comprises an element selected from the group consisting of nickel and mercury.

17. The method of claim 15, wherein said ancillary ligand comprises at least one of $PCy_3$, $P^iPr_3$, $PEt_3$ and $MeNC_5H_4N^iPr$, wherein said Cy is a cyclohexyl group; said $^iPr$ is a isopropyl group; said Et is an ethyl group; said Me is a methyl group; and said $MeNC_5H_4N^iPr$ has the following structural formula:

18. The method of claim 17, wherein said second organometallic compound comprises $Ni(COD)_2$, wherein COD is 1,5-cyclootadiene.

19. The method of claim 18, wherein said organometallic compound comprises an organotin compound having the chemical formula $R_3SnR^1$, wherein:
   a. each of said R is selected from the group consisting of a methyl group and a butyl group; and
   b. said $R^1$ comprises a double bond.

20. The method of claim 1, wherein said step is carried out with a first molar amount of said reagent and a second molar amount of said organic compound, wherein said first molar amount is stoichiometrically equivalent to said second molar amount.

21. The method of claim 20, wherein said first molar amount is greater than said second molar amount.

22. The method of claim 20, wherein said first molar amount is less than said second molar amount.

23. The method of claim 1, wherein said step is carried out at a temperature of between 25° C. to 45° C.

* * * * *